United States Patent [19]

Becker et al.

[11] Patent Number: 5,336,815
[45] Date of Patent: Aug. 9, 1994

[54] PREPARATION OF VINYL GLYCOLS

[75] Inventors: Rainer Becker, Bad Duerkheim; Walter Gramlich, Heidelberg; Michael Huellmann, Heppenheim; Hans-Ulrich Scholz, Weisenheim, all of Fed. Rep. of Germany

[73] Assignee: BASF Aktiengesellschaft, Ludwigshafen, Fed. Rep. of Germany

[21] Appl. No.: 54,819

[22] Filed: Apr. 29, 1993

[30] Foreign Application Priority Data

May 16, 1992 [DE] Fed. Rep. of Germany ....... 4216315

[51] Int. Cl.$^5$ .................... C07C 29/56; C07C 33/035
[52] U.S. Cl. .................... 568/857; 568/807; 568/808; 568/828; 568/838
[58] Field of Search ............. 568/857, 807, 808, 828, 568/838

[56] References Cited

U.S. PATENT DOCUMENTS

| | | | |
|---|---|---|---|
| 3,925,485 | 12/1975 | Chabardes et al. | 568/857 |
| 4,661,646 | 4/1987 | Schalenbach et al. | 568/857 |

FOREIGN PATENT DOCUMENTS

| | | |
|---|---|---|
| 142657 | 5/1985 | European Pat. Off. |
| 1155290 | 4/1958 | France. |

OTHER PUBLICATIONS

Tetrahedron, vol. 45, pp. 7031–7040 (1989).
Houben-Weyl, vol. V/lb, pp. 779, 783, 790 Ed. by Müller (1972).

*Primary Examiner*—Joseph E. Evans
*Attorney, Agent, or Firm*—John H. Shurtleff

[57] ABSTRACT

Preparation of vinyl glycols (I)

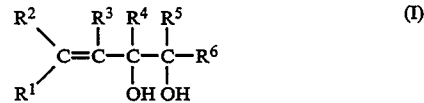

($R^1$ to $R^6$=H, a carbo-organic radical, optionally substituted) in which an unsaturated diol of formula II

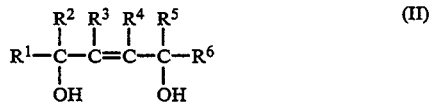

is isomerized in the presence of a rhenium catalyst under neutral conditions. The compounds (I) serve as intermediates for the preparation of active substances and for the preparation of polymers.

7 Claims, No Drawings

PREPARATION OF VINYL GLYCOLS

The present invention relates to an improved process for the preparation of vinyl glycols of the general formula (I)

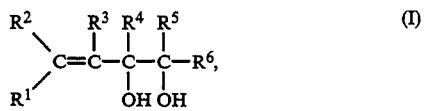

in which the individual radicals $R^1$ to $R^6$ can be the same or different or may be joined together and denote H, $C_1$–$C_{10}$ alkyl, $C_5$–$C_7$ cycloalkyl, $C_7$–$C_{10}$ aralkyl, or a mono- or di-nuclear aryl radical and can themselves carry inert substituents, by isomerization of the corresponding diols of the general formula (II)

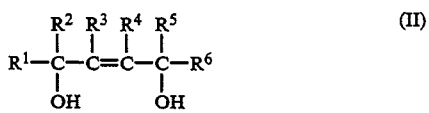

in the presence of catalytically active substances.

The prior art includes the conversion of 2-butene-1,4-diol to vinyl glycol by means of metal catalysts in the presence of acids (EP-A 142,657, Rao et al., *Tetrahedron* 45 (22), 7031 (1989)). However, since vinyl glycols, such as 1-butene-3,4-diol, as secondary allylic alcohols, are very sensitive to acids, undesirable by-products are often formed. In particular, problems arise with the isolation of the products, so that the acid must be neutralized prior to working up the reaction mixture. In the prior art processes the 1-butene-3,4-diol is obtained, moreover, only in yields of up to approximately 60%.

It is thus an object of the present invention to provide an economical process for the preparation of vinyl glycols (I) from unsaturated diols (II).

Accordingly, we have found an improvement on the process defined above, wherein the catalyst used is rhenium or a rhenium compound.

According to the process of the invention, unsaturated diols of the general formula (II) can be isomerized. In said formula the individual radicals $R^1$ to $R^6$ are the same or different. The most preferred substituents are hydrogen and $C_1$–$C_{10}$ alkyl groups, which can be either linear or branched. Preferred alkyl groups are methyl, ethyl, propyl, and butyl groups. Furthermore, $C_5$–$C_7$ cycloalkyl groups are suitable, such as, in particular, a cyclopentyl group or a cyclohexyl group, mono- or di-nuclear aryl radicals, such as naphthyl and in particular phenyl, and $C_7$–$C_{10}$ aralkyl groups, for example, benzyl. The said radicals can themselves carry substituents which are inert under the conditions of the reaction, for example a lower alkyl group or a halogen atom such as chlorine. Furthermore, cyclic unsaturated diols can be used, in which, for example, the radicals $R^3$ and $R^4$ are joined together. Preferably, the ring has from 5 to 7 carbon atoms. Also, this ring can itself be substituted as described above.

The diols II are known in the art or can be obtained by conventional methods. For example, acetylene can be reacted with aldehydes or ketones and the derivatives of 2-butyne-1,4-diol thus obtained are partially hydrogenated catalytically (cf, e.g., *Houben Weyl*, Vol. V/1b, pp. 779, 783, 790, edited by Eugen Mueller, Georg Thieme Verlag, Stuttgart, 1972).

According to the invention, the isomerization of the unsaturated diols to the vinyl glycols (I) is carried out in the presence of rhenium or a rhenium catalyst. Metallic rhenium can be used as rhenium catalyst. It is preferably present in finely divided form, and it can also be used in association with a support. Other suitable catalysts for use in the invention are inorganic and organic rhenium compounds, for example, ammonium perrhenate. Mixtures of different rhenium compounds can also be used. Rhenium heptoxide is most preferably used. Preferably, the isomerization is carried out under neutral conditions, i.e., no acid is added to the reaction mixture. Accordingly, the reaction should be carried out under acid free conditions.

Based on the amount of the diol (II) used, the amount of catalyst employed is usually not less than 10 ppm of Re, calculated as metal. The reaction generally yields the desired products without any problems when the catalyst is used in a concentration of 0.1 wt %. However, it might be necessary to use the catalyst in amounts of up to approximately 1 wt %. Amounts of catalytically active substance of more than 2 wt % generally provide no further improvement.

The isomerization can be carried out without any solvent or in the presence of a solvent; Examples of suitable solvents are $C_5$–$C_{20}$ hydrocarbons such as hexane, cyclohexane, toluene, xylene, or higher-boiling paraffins. Alternatively, halogenated $C_1$–$C_6$ hydrocarbons can be used such as methylene chloride, chloroform, or chlorobenzene. The isomerization of the invention can be alternatively carried out in $C_2$–$C_{12}$ alkyl ethers or $C_2$–$C_{12}$ aryl ethers, such as diethyl ether, tetrahydrofuran, or diphenyl ether. It is equally possible to use a solvent mixture. Alternatively, it might be advantageous to carry out the reaction in the gas phase over a rhenium catalyst. Preferably, the reaction is carried out in the liquid phase.

Generally speaking, the reaction can be carried out at as low a temperature as approximately 20° C. The reaction takes place at an appreciable rate at temperatures above approximately 80° C. However, it might be advantageous to use reaction temperatures of up to approximately 160° C. Reaction temperatures which are higher than about 180° C. are not usually advantageous.

The isomerization reaction can be carried out continuously or batchwise. The preferred procedure is one in which the starting diol (II) is continuously metered to the reaction mixture and the vinyl glycol product (I) is continuously removed from the reaction mixture. In cases where the boiling point of the starting compound (II) is higher than that of the product (I) it has been found to be particularly advantageous to place the rhenium catalyst in the solvent, to reduce the pressure to from approximately 0.01 to approximately 50 mbar and to set the reaction temperature at the corresponding boiling point of the vinyl glycol product (I). While the unsaturated diol is continuously added to the reaction mixture, the mixture can be subjected to continuous fractional distillation. Generally speaking, the distillate thus obtained contains fractions enriched with vinyl glycol product (I) and fractions containing dimerized product. For this reason it is usually advantageous to append a further fractional distillation stage, in order to effect thermal conversion of the dimer to the desired product.

The vinyl glycols are obtained in high purity and in high yields and serve as intermediates for active substances such as vitamin A or as monomers for the preparation of hydrophilic polymers, in particular copolymers.

EXAMPLE

A mixture of 100 g of paraffin oil and 1 g of $Re_2O_7$ was heated to 130° C. After the pressure had been set to approximately 0.5 mbar, 150 g of 2-butene-1,4-diol were added over a period of ca 2 h, and the reaction temperature was kept at 130° C., whilst at the same time the reaction mixture was subjected to distillation There were obtained several fractions having different degrees of enrichment of the product. A further fractional distillation gave 125.1 g of distillate having a content of 1-butene-3,4-diol of 90.8%, which is equivalent to a yield of 76% of theory.

We claim:

1. A process for the preparation of 1-butene-3,4-diol of formula

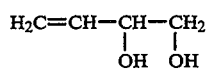   I which comprises: isomerizing 2-butene-1,4-diol of the formula

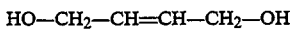   II under acid free conditions in the presence of a catalyst selected from the group consisting of rhenium, a rhenium compound and mixtures thereof.

2. A process as claimed in claim 1, wherein the rhenium catalyst used is rhenium heptoxide.

3. A process as claimed in claim 1, wherein the isomerization is carried out in at least one solvent selected from the group consisting of $C_5$–$C_{20}$ hydrocarbons, halogenated $C_1$–$C_6$ hydrocarbons, $C_2$–$C_{12}$ alkyl ethers and $C_2$–$C_{12}$ aryl ethers.

4. A process as claimed in claim 1, wherein the resulting 1-butene-3,4-diol (I) is continuously removed from the reaction mixture by distillation.

5. A process as claimed in claim 1, wherein the isomerization is carried out at a temperature of about 20° to 120° C., in the liquid phase in the presence of at least one solvent selected from the group consisting of hydrocarbons, halogenated hydrocarbons, alkyl ethers and aryl ethers.

6. A process as claimed in claim 5, wherein the process is carried out at a temperature of from 80° to 160° C.

7. A process as claimed in claim 6, wherein the catalyst is rhenium heptoxide.

* * * * *